United States Patent [19]
Gaafar et al.

[11] 4,186,182
[45] Jan. 29, 1980

[54] SEROLOGICAL TEST FOR *NEISSERIA GONORRHOEAE* ANTIBODIES

[75] Inventors: Hassan A. Gaafar, Voorheesville; Dora D'Arcangelis, Albany, both of N.Y.

[73] Assignee: Research Corporation, New York, N.Y.

[21] Appl. No.: 831,128

[22] Filed: Sep. 7, 1977

Related U.S. Application Data

[60] Continuation-in-part of Ser. No. 674,628, Apr. 7, 1976, abandoned, which is a continuation of Ser. No. 554,061, Feb. 28, 1975, abandoned, which is a division of Ser. No. 385,863, Aug. 6, 1973, abandoned, which is a continuation-in-part of Ser. No. 285,128, Aug. 31, 1972, abandoned.

[51] Int. Cl.² .................... G01N 33/16; A61K 43/00
[52] U.S. Cl. ................... 424/1; 260/112 R; 424/12; 435/7; 435/37
[58] Field of Search ............. 424/1, 12; 195/103.5 A; 260/112 R

[56] References Cited
PUBLICATIONS

Cohen, J. of Bacteriology, vol. 94, No. 1, Jul. 1967, pp. 141–148.

*Primary Examiner*—Benjamin R. Padgett
*Assistant Examiner*—Christine M. Nucker
*Attorney, Agent, or Firm*—Cooper, Dunham, Clark, Griffin & Moran

[57] ABSTRACT

Serological method for determining presence of *Neisseria gonorrhoeae* antibodies in human sera and products utilized in such testing.

23 Claims, No Drawings

SEROLOGICAL TEST FOR *NEISSERIA GONORRHOEAE* ANTIBODIES

RELATED APPLICATIONS

This application is a continuation-in-part of copending application Ser. No. 674,628 filed Apr. 7, 1976, which is, in turn, a continuation of prior pending application Ser. No. 554,061 filed Feb. 28, 1975, which was a division of application Ser. No. 385,863 filed Aug. 6, 1973, which was a continuation-in-part of application Ser. No. 285,128 filed Aug. 31, 1972.

This application also contains material disclosed in the following applications, all of which were filed on Feb. 28, 1975 as divisions of the above identified application Ser. No. 385,863:

Ser. No. 554,087
Ser. No. 554,088
Ser. No. 554,089
Ser. No. 554,090
Ser. No. 554,105;

application Ser. No. 551,983 filed on Feb. 21, 1975 as a continuation of the above identified application Ser. No. 385,863; and application Ser. No. 674,626 filed on Apr. 12, 1976 as a continuation of the above identified application Ser. No. 554,105.

All of the above applications have now been abandoned.

FIELD OF INVENTION

This invention relates to methods and products employed for determining the presence of *Neisseria gonorrhoeae* antibodies in human sera by a serological method.

BACKGROUND OF INVENTION

The present mass screening method for the detection of gonorrhea is a bacteriological method. It requires two to seven days for completion because it necessitates waiting for growth of a colony of gonococcus organisms in an appropriate culture medium and confirmatory biochemical reactions by growth in a fermentation medium, such as shown in Table I. Moreover, the bacteriological method requires that a specimen of the gonorrhea caused discharge arrive at the testing laboratory with the fragile gonococcus organism still viable, a natural time limit of as little as two days. There is real need for improvement.

A serological method which would be capable of detecting antibodies in a blood sample would be highly desirable for use in a mass screening program to demonstrate that an individual may be currently suffering from gonorrhea or had been infected in the past. Individuals reacting positively could then be tested by the bacteriological method to determine if the infection is current. Several serological methods have been reported, but none is completely satisfactory. The primary reason for dissatisfaction has been the low sensitivity and the high number of false positive reactions.

A serological method has now been developed which substantially alleviates the difficulties with known serological techniques, and is suitable for use in mass screening programs as an adjunct to the bacteriological method with substantial elimination of false positive reactions.

THE INVENTION

This invention comprises methods for the detection of gonorrhea produced antibodies and novel products used in the method.

It has now been discovered that *Neisseria gonorrhoeae* (N.g.) organisms produce a species specific antigen which is heat labile and reacts with N.g. produced antibodies in human sera to thereby detect the presence of a past or current gonorrhea infection. The antigen does not react with cross reacting antibodies which may also be present in the sera to cause the false positive reactions which have plagued previously employed serological procedures.

In accordance with the presently preferred testing procedure utilizing suspensions of microorganisms, such a suspension containing the antigen is prepared, and is incubated with two separate samples of sera and tested for the production of an antigen-antibody complex. One sample of serum is heated to inactivate any heat labile cross reacting antibodies which may be present. The other sample is not subjected to heat. The key to the test is that antibodies caused by a gonorrhea infection are heat stable whereas the cross reacting antibodies are heat labile. Therefore, a positive reaction with both of the test samples is a clear indication of the presence of N.g. stimulated antibodies. A negative reaction in both specimens is a clear indication of the absence of such antibodies. A negative reaction with the heated sample coupled with a positive reaction with the unheated sample is an indication of the presence of natural antibodies.

The formation of a positive antigen-antibody complex can be detected by any of the presently available methods. Generally, the procedure is to incubate the complex with a labeled anti-human immunoglobulin, preferably immunoglobulin G (IgG). The heavy chain IgG is preferred. The immunoglobulin can be labeled, for example with a detectable radioactive element, an enzyme or a chemical which fluoresces when exposed to ultraviolet light.

In the presently preferred method described above, separate samples of the antigen containing suspension are placed on a fluorescent antibody slide and incubated with the sera under test, one sample of which is heated, the other unheated. The thus prepared separate specimens are then incubated with an anti-human IgG labelled with fluorescent material such as fluorescein, rhodamine or auramine. The preferred detecting material is, for this method, anti-human IgG conjugated with fluorescein through an isothiocyanate. The product is well known and commercially available.

Basically, the test method of this invention conprises the detection of a conjugate formed by reaction between the N.g. produced heat labile antigen and complementary heat stable antibody. Detection is preferably effected utilizing the reaction with an anti-human IgG labeled with an element or chemical which is detectable by a chemical or physical method. Alternatively, the reaction may be detected by permitting it to take place after the antigen is adsorbed on a carrier. Suitable adsorbents include, for example, various polymer latices such as a polystyrene latex, bentonite or charcoal. The particles comprising antigen adsorbed on an adsorbent are then mixed with the sera to be tested and the presence or absence of flocculation or clumping noted. The sensitivity of this procedure can be enhanced by washing the particles to remove unreacted protein followed by the addition of anti-human IgG. Positive reactions give clumps while in negative reactions the antigen coated particles remain homogeneously dispersed.

A typical agglutination test in which the antigen is adsorbed on charcoal may be conducted as follows:

The antigen is diluted with saline and mixed with an aqueous suspension of fine charcoal particles by adding one volume of charcoal (2.5 mg/ml) to 8 volumes of antigen in a tube. The reagents are mechanically agitated using a Vortex mixer for 5 min. at room temperature and brought to 10 volumes with glycine buffered saline, pH 8.2 (73.1 g glycine, 50 g NaCL, 10 g bovine serum albumin, and 35 ml of 1.0 N sodium hydroxide per 1000 ml).

The sera to be tested are diluted 1:10 in physiological saline and kept at 59° C. for 30 min. The heat-inactivated serum (0.05 ml) is placed in a circle printed on a plastic-surfaced card, and spread within the circle with a wooden toothpick. Sensitized charcoal (0.016 ml), prepared as above, is then added, and the card rotated for 8 min. at 180 rpm, hand-tilted, and left horizontal for 2 min. The results may be read under direct light using a 10X magnifying lens. The agglutination is fine, and any degree of agglutination may be considered positive.

As stated above, the preferred detection method with suspensions is the fluorescent method. However, the anti-human IgG can also be labelled with a radioactive element or with an enzyme. The radioactive label can be detected by any of the currently available counting procedures. The preferred isotope labels are $^{14}C$, $^{131}I$, $^{125}I$ and $^{35}S$. The enzyme label can be detected by any of the presently utilized colorimetric, spectrophotometric, fluorospectrophotometric or gasometric techniques. The enzyme is conjugated to the anti-human IgG by reaction with bridging molecules, such as carbodiimides, diisocyanates, glutaraldehyde and the like. Many enzymes which can be used in these procedures are known and can be utilized. The preferred are peroxidase, B-glucuronidase, B-D-glucosidase, B-D-galactosidase, urease, glucose oxidase plus peroxidase, galactose oxidase plus peroxidase and acid phosphatase.

The optimum sources of antigen for the process of this invention are *Neisseria gonorrhoeae* B-585, B-370 and B-1094. These organisms have been deposited at the American Type Culture Collection, and have received the accession numbers 21823, 21824 and 21825 respectively. Their taxonomic description is:

Order: Eubacteriales
Family: Neissericeae
Genus: Neisseria
Species: *Gonorrhoeae*

Morphology: Gram negative spherical or bean shaped diplococci with adjacent sides flattened usually $0.6 \times 1.0 \mu$ and more uniform in size.

Biochemical and Cultural: Aerobic, optimal growth requires 4-10% $CO_2$ and incubation at 36° C.

The cultures grow slowly on chocolate agar producing small barely visible colonies after 24 hours (0.1 mm in diameter) with typical morphology seen on 48-72 hours cultures. The colonies are small 1.0 mm in diameter, gray white, transparent, smooth, with round entire edge, glistening surface and butyrous consistency. B-1094 produced slightly larger colonies and grows more rapidly.

Oxidase +, catalase +; ferments glucose but not maltose, lactose or sucrose.

Antigenicity: All three isolates share common antigens which have been designated 'L' and are utilized in the practice of this invention.

Virulence: All three strains were originally isolated from patients with symptomatic gonorrhea.

In the process of the invention the sera to be tested is first diluted in physiological saline solution at a dilution of from about 1:2 to 1:1000. The suspension is heated to about 56° C. to 65° C. preferably 59° C. for a period of from about 15 to 40 minutes preferably 30 minutes to inactivate heat labile natural antibodies. The heated serum is then incubated with an antigen produced from a culture of N.g. For the agglutination test, the preferred ratio is at the lower end of the range. For the radioimmunoassay, the preferred ratio is at the higher end of the scale, and for the fluorescence test the preferred ratio is from 1:10 to 1:40.

For the preparation of the antibody slides of this invention, fresh isolates of the N.g. organisms are lyophilized. They are reconstituted as needed and subcultured as needed, on chocolate agar with rabbit blood (Table II) medium. Maintenance cultures in semisolid media (Table III) may be transferred once a month to maintain viability. The cultures are transferred as needed to a suitable growth medium, preferably chocolate agar (rabbit blood) slants, and these are incubated at about 34° C. to 38° C., preferably 35° C. to 37° C. for from about 18 to 24 hours normally in a $CO_2$ (4-10%) atmosphere. The organisms do not grow appreciably at temperatures significantly below 35° C. and die above about 38° C. At periods appreciably below 18 hours the amount of growth is too scarce to be practical, and there is a gradual decline in available antigen after about 24 hours.

Preferably the suspension is checked for purity and typical morphology by Gram staining and streaking on growth medium.

The growth is suspended in physiological saline at a concentration of from about $10^5$ to $10^9$ organisms per ml. For the fluorescence test, the preferred concentration is from $3 \times 10^6$ to $4 \times 10^6$. For the agglutination and enzyme tests, the preferred concentration is of the order of $10^8$ organisms per ml.

A standard antigen slide is a slide preparation where one drop (about 0.05 ml) of a suspension of N.g. organisms in physiological saline at a concentration of $3-4 \times 10^6$ organisms per ml is placed, dried and fixed.

A small drop of the suspension is placed on each end of a cleaned fluorescent antibody slide and smeared with a loop. The slides are air dried, fixed and then rinsed in distilled water to produce a standard antigen slide. The slide is stable after 1 to 3% formalin fixation or without fixing for up to six weeks if maintained at about −20° C. They can be lyophilized and will retain their usefulness for as long as 2 to 3 months at room temperature. The preferred fixative for a refrigerator temperature of about 10° C. is one containing 10% formalin in phosphate buffered saline at pH 7.6, 95% ethanol, and glacial acetic acid in the ratio of 10:90:5. With this reagent the fixed suspension will remain stable for an extended period of time, even more than three months. At refrigeration temperatures, the stability may be enhanced by the presence of a dessicant such as anhydrous calcium chloride.

When utilized in the fluorescent process described above, the antibody slides are stained with diluted samples of the serum to be tested. The serum is diluted at 1:10 to 1:40 with physiological saline. When the serum dilution ratio varies appreciably below this range, the test gives false positives; above the range it gives false negatives. The diluted serum is divided into two aliquots of about 0.5 ml each, and one sample is heated, preferably at 59° C. for 30 minutes.

One drop of the heated diluted serum is added to the suspension on one end of the slide, and a drop of the unheated diluted serum is added to the suspension at the other end of the slide. The slide is then incubated for about 15 to 30 minutes in a humid chamber, preferably one that is saturated with water vapor at from about 22° C. to 37° C.

Upon removal from the chamber, the samples are washed thoroughly in buffered saline to remove serum proteins which are not bound to the antigens or cells. A suitable buffer is the standard phosphate buffer at a pH of 7.5 to 7.7. Washing is preferably accomplished by first dipping several times in the buffer solution, then holding in fresh buffer solution for about 10 minutes, and finally rinsing in millipore $H_2O$. The slide is then dried, suitably by gently blotting with an absorbent paper.

The dried smears are stained with fluorescein isothiocyanate conjugated anti-human IgG for about 20 minutes. The working dilutions for particular conjugate will vary from one lot to the other, and are best determined by titration with known controls. The slides are then mounted, suitably in a glycerol-carbonate-bicarbonate buffer at a pH of from about 8.5 to 9.5, preferably 9.0. Any of a number of mounting fluid compositions can be employed, but they should be selected to have a minimum of autofluorescence.

The degree of fluorescence may be determined with a fluorescent microscope, typically a Leitz fluorescent microscope fitted with an HBO-200 light source, a 3-mm BG-12 exiter filter, a BG-38 red excluding filter, an OG-1 ocular filter, a dark field condenser, and a 100×oil immersion objective.

The fluorescence of the smear stained with the heated serum specimen is compared with the smear stained with the unheated portion of the serum. Specimens that show 1 to 2+ fluorescence or more with the unheated serum with no or insignificant reduction on the heated specimens are considered positive. The determination of fluorescence is somewhat subjective, but an experienced operator will have little or no difficulty distinguishing between positives and negatives.

Lyophilized products from suspensions of N.g. growth cultures, especially N.g. B-585, B-370 and B-1094 are especially valuable sources of antigens. They may be prepared by the following procedure:

A. Prepare concentrated suspensions in sterile milk (100 gr. of skim milk—Baltimore Biological Laboratories—added to 1 l. of water which was preheated to 50° C., sterilize 113° C. to 115° C. for 20 minutes); and then add 5% rabbit or horse blood B. To prepare milk suspension, wash culture slant down with 0.5 ml. milk using a capillary pipette. Dispense 2 drops culture suspension at the bottom of the prenumbered glass tubes.

C. Dispense no more than 0.05 ml. of suspension into the bottom of 6–7×100 mm. cotton-plugged tubes.

D. Remove cotton plug and insert tube in rubber sleeve of connection to vacuum pump, making sure that:

1. Every plug is discarded directly into container for sterilization.

2. Every tube on any one connection contains some culture.

E. Place tubes in bath of dry ice and 95% ethyl alcohol with tilting motion to deposit some of suspension on glass a few millimeters above major part of material to be dried.

F. Until connected to the manifold of the pump and the pressure is satisfactory for rapid drying, keep cultures in, or so near freezing bath, that no thawing can occur.

The lyophilized products are characterized by the presence of a species specific, heat labile antigen which will react with a heat stable N.g. antibody in patients' sera to form an antigen-antibody complex. They are especially valuable because they can be used in any of the variations of the test procedures described herein. They can, for example, be taken up in physiological saline and the suspension used in the fluorescent procedure described above. They are also valuable in the enzyme and radioactive techniques, as will be readily apparent to those skilled in the art.

The adaptation of the process of this invention to an enzyme testing technique with cell suspensions is accomplished by labelling the anti-human IgG with an enzyme such as horseradish peroxidase. The antigen-antibody conjugate is prepared for a sample of heated serum and antigen suspension as described above. The sample is incubated with the labelled anti-human IgG and washed to remove extraneous protein. The washed product is mixed with a substrate such as o-dianisidine and hydrogen peroxide. After about 3 to 5 minutes, the reaction is stopped by the addition of a few drops of 6 N sulfuric acid. The optical density is measured at 400 mm. Reactive sera is indicated by a higher optical density than similarly treated negative controls.

Other acids can be used to arrest the reaction, for example hydrochloric acid. In that event, the preferred reading for optical density may be other than 400 mm.

In the radioimmunoassay procedure anti-human IgG is labelled with the selected isotope according to standard procedures, reacted with the antigen-antibody complex and the product counted using, for example, an autogamms spectrophotometer.

The methods of this invention are applicable to antigenic cell suspensions with an antigen unit value, as defined below of at least 100. With cell suspensions, the preferred procedure is the fluorescence method which, when utilized as described above, depends upon the morphology of the cells,—as will be recognized by those skilled in the art.

In another, and more preferred, embodiment of this invention, purified antigens or antigenic compositions are employed. With these materials, all of the general methods described above are also applicable. The use of purified antigens or antigenic compositions is preferred over the use of cell suspensions because the results are generally more reproducible and the procedures are more easily automated. Moreover, the fluorescence procedure, when applied to these materials, is not subjective as in the case of cell suspensions, but rather it is objective since the results are determined by comparisons with controls containing known concentrations of antigens and antibodies.

In the presently preferred procedure for purification of the antigen and for the preparation of antigenic compositions, the selected N.g. strains are grown on a suitable media, preferably Rabbit chocolate agar. The cell growth is suspended in physiological saline solution and filtered through sterile gauze. During this and all subsequent manipulations involving the antigen or fractions containing the antigen, unless noted otherwise, the solutions, suspensions, etc. are kept cold at about 5° C. to 10° C.

The residue on the filter is washed with physiological saline and centrifuged at about 10,000 RPM for about 15 minutes. The centrifuged material is decanted and the supernatant liquid discarded. The sediment is resuspended in physiological saline, pooled and washed by centrifugation.

The antigen may be extracted with cationic detergents such as sodium lauryl sulfate (SDS), sodium deoxycholate, sodium cholate or similar materials.

As is common with complex natural materials, antigens used in this invention may differ slightly in chemical and physical properties depending upon the source and the method of isolation and purification. The following characteristics, however, are common:

1. Species specificity.
2. Protein in nature and inactivated by proteolytic enzymes such as trypsin.
3. Stable in aqueous media at pH values of 3–11.
4. Heat labile in aqueous media; partially inactivated by heating at about 56° C. for 30 minutes and completely inactivated by boiling for 1 h.
5. Contains no deoxynucleic or ribonucleic acid as evidenced by stability when incubated with the corresponding enzymes.
6. Not affected by dextranase.
7. Not affected by neuraminidase.
8. Acidic with an isoelectric point of about $4.0 \pm 0.2$.
9. A molecular weight of antigenically active subunits of 37,000–40,000 as determined by SDS -polyacrylamide gel.
10. Contains 1–10% carbohydrate and 2–3% organic phosphorous.
11. Soluble in aqueous media at low concentration and solubility increases in the presence of surface active agents, but insoluble in methanol, chloroform, and acetone.

While the purified antigen can be prepared by the procedures described above, and can be used in the process of this invention, it is not necessary, nor is it preferred to do so. The reason for this is that antigenic compositions containing even relatively high quantities or impurities such as extraneous protein can be used.

The antigenic activity of a particular composition can be defined in terms of antigen units by reference to the standard antigen slide as defined above. The method of determining antigen units will require some explanation. It is based on the ability of a particular composition to inhibit the preferred fluorescent test which is used with cell suspensions, and is described in detail above.

As described above, the fluorescent test with cell suspensions depends upon the morphology of the cells. More particularly, it depends upon the morphological localization of the antigen on the intact cell. Optimum conditions for the test prevail when the complete cell is intact. During the course of purification in accordance with this invention, more and more antigen is cleaved from the cells. The compositions thus become less and less suitable for the type of fluorescent testing which depends upon cell morphology.

In the initial stages of purification, there will be relatively large amounts of protein, for example, cellular debris, which is not antigenic in nature in the compositions. This material does not contribute to the antigen unit values. With increasing purification, the extraneous protein is removed and the antigen unit values increase rapidly.

With careful purification, it is possible to obtain products with antigen unit values of 10–20,000 units per mg. of protein, or even higher. However, products with values of at least 100 can be used in fluorescent testing, enzyme testing, radioimmunoassay and agglutination procedures to determine the presence of N.g. antibodies in human sera. It is preferred, however, that the values be at least 1000.

The following definitions will be helpful in understanding this aspect of the invention:

Conjugate Unit (C.U.)

This is the lowest concentration of fluorescein conjugated anti-human IgG in saline (w/v) which when added in aliquots of 0.05 ml to a standard antigen slide preparation stained with excess specific antibodies will give a 4+ fluorescence.

Antibody Unit (Ab.U.)

It is the highest dilution of heat inactivated serum in physiological saline (w/v) which gives a 4+ fluorescence when used to stain standard antigen slides and counter stained with fluorescein conjugated anti-human IgG appropriately diluted to contain 2 conjugated units in 0.05 ml.

Antigen Unit (Ag.U.)

One Antigen Unit (Ag.U.) is defined as that amount of a whole, partially purified, or pure antigen preparation, expresses as $\mu$g protein, which when allowed to react with heat inactivated serum diluted to contain one Ab.U./0.05 ml will adsorb this unit of activity and when this adsorbed serum is used to stain the standard antigen slide and counter stained with fluorescein conjugated anti-human IgG appropriately diluted to contain 2 C.U./0.05 ml will give fluorescence of shadow to 1+. An antigen unit is the minimum amount of material which will absorb one antibody unit.

It will be appreciated that the purity of an antigen proteinaceous preparation is directly proportional to the number of antigen units per mg. of protein.

The antigen compositions of this invention can be used in all of the tests described above in connection with cell or organism suspensions. The procedures will be generally the same. For example, the antigen composition can be reacted with the N.g. antibody in test sera on a slide, and the resulting complex incubated with IgG labelled with a fluorescent chemical. Alternatively, the IgG may be labelled with any of the enzymes or isotopes mentioned above. The procedure for the agglutination test described above is the same, except that the suspensions are replaced with purified antigens or antigenic compositions.

As stated and described above, antigens or antigenic compositions of this invention are particularly useful when conjugated or adsorbed on particulate carriers or substrates. Such materials do not affect the antigen-antibody reaction.

Neither do they affect the subsequent reaction with the labelled compound. As stated, any of a very wide variety of carriers can be employed, including polymeric materials such as polystyrene, inorganic materials such as glass, silica, bentonite or charcoal, and cellulosic materials such as Sepharose, Sephadex or cellulose.

Biological carriers such as red blood cells may also be employed.

In one procedure for the conjugation of species specific N.g. antigens to non-antigenic carriers, equal volumes of the partially purified or pure antigen preparations containing at least 100 Ag.U./mg of protein and the selected carrier, for example, DEAE-cellulose in 0.1 m phosphate buffer at pH 8 are mixed and refrigerated overnight. The particles are recovered by filtration and washed with additional buffer solution, for example, 0.3 m phosphate buffer at pH 7.0, and again with 0.1 m phosphate buffer at pH 7 with 1% albumin. The washed conjugate is resuspended in 0.1 m phosphate buffer at pH 7 with 1% albumin in a volume equal to the volume of the original antigen solution.

The antigen-carrier conjugate may be used in enzyme immunoassay or radioimmunoassay in the manner described above. It has been observed that when these conjugates are employed in the testing procedures there is less background interference in the reading of the testing instruments with resulting better differentiation between positive and negative tests.

A wide variety of tests have been described based upon incubating the heat labile antigen compositions of this invention with heated sera to be tested and determining the presence of an antigen-antibody conjugate as an indication of a positive reaction. Modifications of the tests described, and other tests will be apparent to those skilled in the art. All are based on the discovery of the species specific antigenic compositions of this invention coupled with the observation that cross-reacting antibodies present in infected sera may be inactivated by heating.

The following non-limiting examples are given by way of illustration only.

EXAMPLE 1

INDIRECT IMMUNOFLUORESCENT ANTIBODY TEST

Preparation of the Antigen

1. Fresh isolates of *N. gonorrhoeae* with appropriate antigen profile or a lyophilized subculture of the standard strains (B-370, B-585 or B-1094) are subcultured to maintenance medium (Table III). The cultures are maintained at 37° C. in a 4–10% $CO_2$ atmosphere and subcultured to fresh maintenance medium once a month.
2. The strains are subcultured as needed to freshly prepared chocolate agar slants (rabbit blood) (Table II).
3. The slants are incubated at 36° C. for 18–24 hours and the growth is suspended in physiological saline and adjusted to $3-4 \times 10^6$ organisms/ml.
4. A small drop of the suspension is placed on each end of an alcohol cleaned fluorescent antibody slide and smeared with a loop.
5. Slides are air dried and fixed in 1% formalin for 10 minutes.
6. Slides are rinsed 10× in distilled water, air dried and stored in −20° C. until needed.

Preparation of the Patient's Serum

1. Dilute patient's serum 1:10 in physiological saline.
2. 0.5 ml. of the 1:0 dilution is heated for 30 minutes in a 59° C. water bath.

Staining

1. Slides are taken out of the freezer 10—15 minutes before use and labelled with patient's name or number.
2. Add one drop of heated diluted serum to one end of the prepared antigen slides and one drop of the unheated serum to the other end.
3. Allow to incubate at room temperature for 20 minutes in a humid chamber.
4. Wash 10 times rapidly in 0.1 M phosphate buffered saline pH 7.6.
5. Wash for 10 minutes in a fresh bath of the same buffer.
6. Rinse 10 times in distilled water and gently blot dry.
7. Stain with working dilution of fluorescein isothiocyanate conjugated anti-human immunoglobulin G for 20 minutes followed by a washing cycle as before (steps 4 to 6).
8. Mount the slides in a glycerol-carbonate bicarbonate buffer pH 9.0

Readings

The slides are examined with a fluorescent microscope fitted with an HBO-200 light source, 3 mm BG-12 exciter filter, a BG-38 red excluding filter, and OG-1 ocular filter, a dark field condenser, and a 100× oil immersion objective.

Interpretation of Results

The degree of the peripheral fluorescence of the bacterial cells in the smear stained with the heated serum specimen is compared with the smear stained with unheated serum. Specimens that show 1–2+ fluorescence or more with nor or insignificant reduction after heating, are considered positive and interpreted to indicate current or recent past infection.

EXAMPLE 2

COLORIMETRIC ENZYME-LINKED IMMUNOASSAY

Preparation of the Antigen

1. Fresh isolates of *N. gonorrhoeae* with appropriate antigenic profile or a lyophilized subculture of the standard strains (B-370, B-585 or B-1094) are subcultured to maintenance medium (Table III). The cultures are maintained at 37° C. in a 4–10% $CO_2$ atmosphere and subcultured to fresh maintenance medium once a month.
2. The strains are subcultured as needed to freshly prepared chocolate agar slants (rabbit blood) (Table II).
3. The slants are incubated at 36° C. for 18–24 hours and the growth is suspended in physiological saline and adjusted to $3-4 \times 10^8$ organisms/ml.
4. Rabbit IgG in 0.1 M phosphate buffered pH 7.0 is added to the bacterial suspension to a final concentration of 50 mg/ml.
5. Aqueous solution of 2.5% gluteraldehyde is added dropwise with gentle stirring to a final concentration of 10 mg. gluteraldehyde per 100 mg. protein in solution.
6. Leave at room temperature for 1 hour.
7. Disperse the insoluble protein-bacterial gel in 0.2 M phosphate buffered saline pH 7.2.
8. Centrifuge for 15 minutes at 3000 rpm at 4° C.
9. Repeat steps seven and eight two times.

10. Resuspend the protein-bacterial gel in a volume of 0.2 M phosphate buffered saline pH 7.2 four times the volume of the rabbit protein added in step 4.

11. Dispense the suspension in 0.25 ml. of aliquots and store in refrigerator until used.

Preparation of the Patient's Serum

1. Dilute patient's serum in 0.2 M phosphate buffered saline pH 7.2. 1:10, 1:100, and 1:1000.

2. Heat the different dilutions for 30 minutes in a 59° C. water bath.

Procedure

1. Add 0.25 ml. of each dilution to the antigen preparation in separate tubes and mix by shaking manually.

2. Incubate at 37° C. for 15 minutes in a water bath.

3. Centrifuge at 3000 rpm for 5 minutes and discard the supernatant.

4. Wash the pellet 2 times with 5 volume of 0.2 M PBS pH 7.2.

5. Add 0.1 ml. of working dilution of horseradish peroxidase (HRP) conjugation anti-human immunoglobulin G.

6. Incubate at 37° C. for 15 minutes in a water bath.

7. Add 5.0 ml. of 0.2 M PBS pH 7.2, centrifuge and wash the pellet as before (steps 5 and 6).

8. Add 3.0 ml. of the substrate (Table IV) and mix by shaking.

9. After 5 minutes the reaction is stopped by adding one drop of 6 N sulfuric acid.

10. The O.D. is measured at 400 mm.

Interpretation

Reactive sera are indicated by comparison with a standard curve prepared with known positive and negative sera.

Controls runs with each batch should include:
(a) Positive controls
(b) Negative controls
(c) Weekly positive (bordenline controls)
(d) Antigen control
(e) Substrate control
(f) Enzyme control

EXAMPLE 3

ENZYME - LINKED IMMUNOASSAY

Preparation of Antigen

1. Fresh isolates of *N. gonorrhoeae* with appropriate antigenic profile or a lyophilized subculture the standard strains (B-370, B-585 or B-1094) are subcultured to maintenance medium (Table III). The cultures are maintained at 37° C. in a 4–10% $CO_2$ atmosphere and subcultured to fresh maintenance medium once a month.

2. The strains are subcultured as needed to freshly prepared chocolate agar slants (rabbit blood) (Table II).

3. The slants are incubated at 36° C. for 18–24 hours and the growth is suspended in physiological saline and adjusted to $3-5 \times 10^8$ organisms/ml.

4. Store the suspension in the refrigerator until used.

Preparation of Patient's Sera

1. Dilute patient's serum in 0.2 M phosphate buffered saline pH 7.2. 1:10, 1:100 and 1:1000.

2. Heat the different dilutions for 30 minutes in a 59° C. water bath.

Procedure 1. 0.2 ml. of the bacterial suspension is placed on a disposable filter.

2. 0.2 ml. of the patient's serum is added and mixed with cells by manual shaking.

3. Incubate at 37° C. for 15 minutes.

4. Wash thrice by suction using 5.0 ml. of 0.2 M PBS pH 7.2.

5. Add 0.1 ml. of working dilution of horseradish peroxidase conjugated anti-human immunoglobulin G.

6. Incubate at 37° C. for 15 minutes.

7. Wash as in step 4 and check the final washing for enzyme activity and repeat the washings if necessary.

8. Add 1.0 ml. of the substrate. The substrate is prepared by adding 1.0 ml. of 30% hydrogen peroxide to 99 ml. of distilled water to form a 0.3% solution. This solution (1 ml.) is added to 99 ml. of 0.01 M phosphate buffer pH 6.0 (0.003%) and 0.2 ml. of 1% o-dianisidine in methyl alcohol is added to 24.0 ml. of thus prepared 0.003% hydrogen peroxide.

9. Reactive sera give reddish-brown pigmentation of the filter.

EXAMPLE 4

PREPARATION OF ANTIGENIC COMPOSITIONS

The cell growth from step 2 of Example 1 above is harvested and suspended in physiological saline solution. It is then filtered through cheesecloth at a temperature of 5°–10° C., which temperature is maintained throughout subsequent manipulations. The residue on the filter is washed twice with physiological saline solution and the filtrate centrifuged at 10,000 rpm for 10 minutes. The sediment is resuspended in physiological saline and washed once by centrifugation. The sediment containing the antigen is weighed to calculate the wet weight.

A total of 6.0 ml. of 0.3% SDS in physiological saline is added to the precipitate from the centrifugation per gram of wet weight of bacterial sediment, and the mix is incubated at room temperature for 10 minutes. The mix is centrifuged at 10,000 rpm for 10 minutes and the supernatant collected. The sediment is treated with 6.0 ml/gm. of 0.1% SDS in physiological saline. The mix is incubated at room temperature for 10 minutes, centrifuged as before, and a second supernatant collected. The two supernatants are recentrifuged to remove any cells or large fragments and pooled.

At this point, the antigen unit value is 100–200 Ag. u./mg of protein.

The pooled supernatant is column chromatographed over Sepharose 4B and eluted with 0.002 molar phosphate buffer at pH 7.6. Appropriate fractions (usually 5–10 ml) are collected and the protein concentration monitored by the Lowry technique. The antigen composition with the best Ag. u. value is found in the first peak which is made up of 5–10% of the protein. With fresh preparations, the value is from 1000–2000 Ag. u./mg.

EXAMPLE 5

CONJUGATION TO NON-ANTIGENIC CARRIER

Equal volumes of antigen solutions containing a minimum of 100 Ag. u./mg. of protein and DEAF-cellulose in 0.1 molar phosphate buffer at pH 8 are mixed and left standing overnight in the refrigerator. The mix is filtered and washed 3 times with an equal volume of 0.3 molar phosphate buffer at pH 7 followed by an additional 3 washings with equal volumes of 0.1 molar phosphate buffer at pH 7 with 1% albumin. The washed conjugate of antigen to cellulose is resuspended in 0.1 molar phosphate buffer at pH 7 with 1% albumin in a volume equal to that of the original solution.

This material is suitable for use in any of the various testing procedures described above.

EXAMPLE 6

Colorimetric Enzyme-linked Immunoassay with Antigenic Composition

For each sample of patient's serum to be tested, an 0.6 micron filter is first wet with 0.1 molar phosphate buffer at pH 7 with 1% albumin. A total of 0.5 ml. of patient's serum (1:10 dilution) is added together with 0.2 ml. of the final suspension from Example 5. The mix is incubated at room temperature for 60 minutes and washed thoroughly 6 times with the same phosphate buffer.

A total of 0.2 ml. of the appropriate dilution of horseradish peroxidase (HRP) conjugated with anti-human IgG is added followed by 4.0 ml. of the same buffer. The mix is incubated for 30 minutes at room temperature and washed until the filtrate is free of conjugate.

The filter with the precipitate is placed in a test tube containing the substrate (Table IV) and incubated for 5 minutes. The reaction is then stopped by the addition of 2 drops of 6 N sulfuric acid. The optical density of the solution is read at 400 manometers. The test results are interpreted by comparison with controls which are known to be positive or negative.

EXAMPLE 7

COLORIMETRIC ENZYME-LINKED IMMUNOASSAY

1. Mix 1 gram of cyanogen bromide activated Sepherose IV particles (CNB-Sepherose activated-Pharmacia Fine Chemicals) with 5 ml. portions of $10^{-3}$ M. HCl.
2. Pour the fraction containing at least 100 Ag. u./mg. of protein onto the filter bed and recycle filtrate several times until the protein is adsorbed maintaining at all times a temperature of 5°–10° C.
3. Block any remaining active sites on the Sepherose by adding 5–10 ml. of 0.5% Bovine Serum Albumen in 1 M. glycine buffer (pH 8.2), recirculate filtrate overnight by continuous pumping.
4. Let filtrate drain out and transfer adsorbed particles to centrifuge, suspend in 10 ml. saline solution, centrifuge at about 10,000 rpm for 10 minutes. Decant and discard supernatant liquid.
5. Repeat washing as in step 4 and recover precipitate.
6. Suspend particles in about 10 ml. of saline solution.
7. Dilute patient's serum one to ten.
8. Mix 0.1 ml. of particle suspension (from 6) with 0.5 ml. of the diluted serum.
9. Incubate at room temperature for 45 minutes.
10. Centrifuge at about 5000 rpm for 10 minutes at room temperature. Discard supernatant liquid.
11. Resuspend the precipitate in 0.1 ml. of rabbit anti-human IgG conjugated through gluturaldehyde to horseradish peroxidase. (50 micrograms protein per ml.)
12. Incubate 30 minutes at room temperature.
13. Centrifuge at 5000 rpm for 10 minutes and discard supernatant.
14. Wash precipitated particles twice by centrifugation at in 13 with 0.01 M phosphate buffer, pH 7.0.
15. To the Washed precipitate, add 2 ml. of the substrate mixture of Table IV.
16. Incubate for 15 minutes at room temperature.
17. Add 2–3 drops of 6 N sulfuric acid to stop reaction.
18. Measure adsorption at 4000 Angstroms (400 mm) using a Gilford 2400 instrument.

A positive serum will give a reading of about 100, a negative serum of about 40.

The following Tables illustrate the variou media utilized in the description of this invention.

TABLE I

FERMENTATION MEDIUM

Starch gelatin agar, infusion-free, with indicator and carbohydrate (for *Neisseria gonorrhoeae* and *Neisseria meningitidis*)

| | |
|---|---|
| Agar | 6 grams |
| Gelatin | 10 grams |
| Sodium chloride | 5 grams |
| Peptone (Difco proteose No. 3) | 10 grams |
| Starch, soluble, powdered | 5 grams |
| Water to Make | 1000 grams |
| Phenol red, 0.02 percent | 30 ml. per kg. |
| Carbohydrate (Sucrose, Glucose or Maltose) | 10 grams per kg. |

Dissolve the agar in half the water by autoclaving; the gelatin, salt, peptone, and starch in the remainder with heat. Combine and make up to total weight. Adjust pH to 7.4–7.6. Filter through cotton. Weigh the filtrate recovered and add the indicator and carbohydrate. Dispense 2.5 ml. amounts in 11 by 75 mm. tubes and autoclave at 115° C. for twelve minutes. Trim the plugs and seal with paraffin.

TABLE II

GROWTH MEDIUM

Glucose agar, infusion free, with coagulated blood (for *Neisseria gonorrhoeae* and *Neisseria meningitidis*)

| | |
|---|---|
| Agar | 15 grams |
| Sodium chloride | 5 grams |
| Disodium phosphate, $Na_2HPO_4$ | 5 grams |
| Peptone, (Proteose peptone #3) | 20 grams |
| Glucose | 0.5 grams |
| Distilled water to make | 1000 grams |
| Rabbit blood, defibrinated, sterile | 10 ml. per 100 |

Dissolve the agar in half the water by autoclaving; the salts, peptone, and glucose in the remainder with heat. Combine and make up to 1 kg. and adjust pH to 7.4–7.6. Dispense 1500 ml. amounts in 3 L gauged neck flasks. Autoclave thirty minutes. Store.

As required, melt the agar base. Admix the blood aseptically 15–20 ml. amounts in glass-covered Petri plates. Deliver without incubation.

TABLE III

MAINTENANCE MEDIUM

Beef-infusion agar with ascitic fluid

| | |
|---|---|
| Beef infusion, concentrated | 500 grams |
| Agar | 5 grams |
| Sodium chloride | 5 grams |
| Peptone | 10 grams |
| Water | 500 grams |
| Ascitic fluid, sterile | an equal volume |

Dissolve the agar in the water by autoclaving, and the peptone and salt in the infusion. Combine. Make up to total weight. Adjust pH to 7.5 with 1 N NaOH. Filter by asperation. Usually dispense 400 ml. amounts in 2 liter flasks and autoclave thirty minutes. Store. Melt the agar base and cool to 50° C.

Warm the ascitic fluid to 50° C. and combine aseptically. Mix well and dispense with aseptic precautions 4-6 ml. amounts in 15 by 125 mm. tubes. Cover the medium aseptically with about 4 ml. of sterile mineral oil. Cool in an upright position. Incubate forty-eight hours at 35° C.-57° C. and ninety-six hours at 20° C.-27° C. Inspect and store.

TABLE IV
SUBSTRATE FOR PEROXIDASE TEST (a) Dilute 3% hydrogen peroxide solution with water to make a one to one hundred dilution.
(b) Dilute the solution with phosphate buffer (0.01 molar at pH 7) to another one to one hundred dilution.
(c) To 24 ml. of the thus diluted hydrogen peroxide, add 0.2 ml. of a 1% solution of O-anisidine in methanol.

What is claimed is:

1. A serological method for determining the presence of Neisseria gonorrhoeae antibodies in human serum which comprises diluting the serum to be tested in physiological saline at a dilution of about 1:2 to 1:1000, heating the diluted serum at about 56° C. to 65° C. for from about 15 to 30 minutes and thereafter incubating with a composition containing a heat labile, species specific antigen produced from a growth culture of Neisseria gonorrhoeae to form an antigen-antibody conjugate when said antibodies are present and detecting the presence of said conjugate; the antigen being protein in nature and characterized as follows:
    1. partially inactivated by heating at about 56° C. for about 30 minutes and completely inactivated by boiling for 1 h,
    2. stable in an aqueous medium at pH values of 3-11,
    3. stable when incubated with the following enzymes:
        deoxynucleic acidase
        ribonucleic acidase
        dextransase
        meuraminidase
        lysosyme,
    4. inactivated when incubated with trypsin,
    5. isoelectric point of 4±0.2,
    6. molecular weight of active subunits of 37,000-40,000 as determined by SDS-polyacrylamide gel,
    7. contains 1-10% carbohydrate and 2-3% organic phosphorus, and
    8. soluble in acqueous media containing surface active agents, and insoluble in methanol, chloroform, and acetone.

2. A serological method as in claim 1 wherein the presence of said conjugate is detected by reaction with an anti-human IgG labelled with a chemical which fluoresces when exposed to ultraviolet light.

3. A method as in claim 2 wherein the chemical is selected from the group consisting of fluorescein, rhodamine and auramine.

4. A method as in claim 2 wherein the antigen composition has an antigen unit value of at least 100 Ag. u./mg. of protein.

5. A method as in claim 2 wherein the antigen unit value is at least 1000.

6. A method as in claim 2 wherein the antigen is produced by a culture of Neisseria gonorrhoeae ATCC No. 21823.

7. A method as in claim 2 wherein the antigen is produced by a culture of Neisseria gonorrhoeae ATCC No. 21824.

8. A method as in claim 2 wherein the antigen is produced by a culture of Neisseria gonorrhoeae ATCC No. 21825.

9. A serological method as in claim 1 wherein the presence of said conjugate is detected by reaction with an antihuman IgG labelled with an enzyme.

10. A method as in claim 9 wherein the enzyme is selected from the group consisting of peroxidase, B-glucuronidase, B-D-glucosidase, B-D-galactosidase, urease, glucose oxidase plus peroxidase, galactose oxidase plus peroxidase, and acid phosphatase.

11. A method as in claim 9 wherein the antigen composition has an antigen unit value of at least 100 Ag. u./mg. of protein.

12. A method as in claim 9 wherein the value is at least 1000.

13. A method as in claim 9 wherein the antigen is produced by a culture of Neisseria gonorrhoeae ATCC No. 21823.

14. A method as in claim 9 wherein the antigen is produced by a culture of Neisseria gonorrhoeae ATCC No. 21824.

15. A method as in claim 9 wherein the antigen is produced by a culture of Neisseria gonorrhoeae ATCC No. 21825.

16. A serological method as in claim 1 wherein the presence of said conjugate is detected by reaction with an antihuman IgG labelled with a radioactive element.

17. A method as in claim 16 wherein the radioactive element is selected from the group consisting of $^{14}C$, $^{125}I$, $^{131}I$, and $^{35}S$.

18. A method as in claim 16 wherein the chemical is selected from the group consisting of fluorescein, rhodamine and auramine.

19. A method as in claim 16 wherein the antigen composition has an antigen unit value of at least 100 Ag. u./mg. of protein.

20. A method as in claim 16 wherein the antigen unit value is at least 1000.

21. A method as in claim 16 wherein the antigen is produced by a culture of Neisseria gonorrhoeae ATCC No. 21823.

22. A method as in claim 16 wherein the antigen is produced by a culture of Neisseria gonorrhoeae ATCC No. 21824.

23. A method as in claim 16 wherein the antigen is produced by a culture of Neisseria gonorrhoeae ATCC No. 21825.

* * * * *